United States Patent [19]

Sato et al.

[11] Patent Number: 4,478,082

[45] Date of Patent: Oct. 23, 1984

[54] METHOD AND APPARATUS FOR DETECTING RUBBING IN A ROTARY MACHINE

[75] Inventors: Ichiya Sato; Takao Yoneyama; Tsuguaki Koga; Kazuo Ikeuchi; Katsukuni Hisano, all of Hitachi, Japan

[73] Assignee: Hitachi, Ltd., Tokyo, Japan

[21] Appl. No.: 408,949

[22] Filed: Aug. 17, 1982

[30] Foreign Application Priority Data

Aug. 26, 1981 [JP] Japan ........................... 56-132799

[51] Int. Cl.³ ..................... G01H 1/00; G01M 13/00
[52] U.S. Cl. .................................. 73/593; 73/660
[58] Field of Search ............... 73/587, 593, 658, 659, 73/660

[56] References Cited

U.S. PATENT DOCUMENTS 3,012,434  12/1961  Wehof ................................. 73/660
3,307,408  3/1967   Thomas et al. ...................... 73/462
3,400,578  9/1968   Frarey et al. ........................ 73/660
4,377,947  3/1983   Matsushita et al. ................. 73/593

FOREIGN PATENT DOCUMENTS

124064  9/1980  Japan ................................. 73/587
729901  5/1955  United Kingdom ................. 73/462

*Primary Examiner*—James J. Gill
*Attorney, Agent, or Firm*—Antonelli, Terry & Wands

[57] ABSTRACT

A method and apparatus for detecting the occurrence of rubbing in a rotary machine, in which at least one acoustic sensor is mounted on at least the rotor part or the stator part of the rotary machine, and the output signal from the acoustic sensor is detected and then filtered to extract a frequency component having a frequency substantially equal to the rotational frequency of the rotary machine, so as to detect the occurrence of rubbing in the rotary machine as early as possible and also to locate the source of the rubbing. Even when the occurrence of abnormal metal-to-metal contact at a bearing of the rotary machine is detected, it is discriminated from rubbing so that the occurrence of the rubbing can be reliably detected.

4 Claims, 13 Drawing Figures

FIG. 7A
NORMAL

FIG. 7B
RUBBING (R)

FIG. 7C
ABNORMAL
METAL CONTACT (C)

FIG. 7D
R AND C

FIG. 9

| SITUATION / OUTPUT WAVEFORM | NORMAL | RUBBING (R) | METAL CONTACT (C) | R AND C |
|---|---|---|---|---|
| (I) AMPLIFIER 25 | | | | |
| (II) DETECTOR 26 | | | | |
| (III) ROTATION TUNED FILTER 29 | | | | |
| (IV) RECTIFIER 31a | | | | |
| (V) BAND-PASS FILTER 33 | | | | |
| (VI) RECTIFIER 31b | | | | |
| (VII) COMPARATOR (VI)−(IV) 34 | | | | |

FIG. 10

METHOD AND APPARATUS FOR DETECTING RUBBING IN A ROTARY MACHINE

This invention relates to a method and apparatus for detecting the occurrence of so-called rubbing in a rotary machine, such as a steam turbine or a turbine-driven generator, due to mechanical contact of its rotor with its stator during rotation of the rotary machine.

In the past, the occurrence of rubbing in such a rotary machine could only be primitively detected, since the ear of a machine operator sensitive to sound was relied upon to hear the vibration sound generated due to the occurrence of rubbing. On the other hand, an apparatus for detecting bearing trouble in such a rotary machine has been proposed and is already known, which apparatus comprises a temperature sensor mounted on each of the bearings for sensing variation of the temperature of the associated bearing. However, this apparatus could not detect the occurrence of rubbing, and, in view of a considerable length of time required until the temperature of the bearing rises up to the level sensed by the temperature sensor, it has been difficult to detect the bearing trouble in the early stage in which the degree of burn damage to the bearing is not serious.

Also, Japanese Patent Application No. 54-128918 (filed Oct. 8, 1979 and corresponding to U.S. patent application Ser. No. 195106) assigned to the assignee of the present application discloses an apparatus for detecting the so-called metal wipe phenomenon which tends to occur during preparatory conditioning run of such a rotary machine, that is, during turning at a low rotational speed. However, the disclosed apparatus is unable to detect the occurrence of rubbing in the rotary machine.

It is therefore an object of the present invention to provide a method and apparatus for detecting the occurrence of rubbing in a rotary machine, such as a steam turbine or a turbine-driven generator.

Another object of the present invention is to provide a method and apparatus of the above character which can also locate the source of occurred rubbing and can reliably detect the occurrence of rubbing while discriminating it from bearing trouble which may occur simultaneously in one of the bearings of the rotary machine.

The above and other objects, features and advantages of the present invention will be more clear from the following detailed description with reference to the accompanying drawings, in which.

The present invention is based on the finding that, when an acoustic sensor is mounted on a bearing of a rotary machine, such as a steam turbine or a turbine-driven generator, to sense a high-frequency acoustic signal transmitted to the bearing, and the output signal from the acoustic sensor is detected by a detector and is then subjected to frequency analysis, a frequency component having a frequency equal to that of the rotational speed (the number of revolutions) or rotational frequency of the rotary machine provides the principal component of the high-frequency acoustic signal in the event of the occurrence of rubbing between the rotor and stator of the rotary machine. Therefore, when the detector output signal is passed through a band-pass filter controlled by the rotational frequency of the rotary machine, a rubbing signal having a waveform analogous to the sinusoidal waveform can be extracted when rubbing is present, so that the presence or absence of rubbing can be easily detected. According to the present invention, a plurality of such sensors are disposed on a plurality of bearings respectively of the rotary machine so as to detect the location of the rubbing, if any, occurring between the rotor and stator of the rotary machine by detecting and filtering the output signals from the sensors. Further, according to the present invention, even when an abnormal acoustic signal such as a noise signal may be simultaneously generated due to the occurrence of abnormal metal-to-metal contact at any one of the bearings, the occurrence of rubbing can be reliably detected by the provision of means for discriminating between the rubbing signal and the noise signal.

Figure 1:
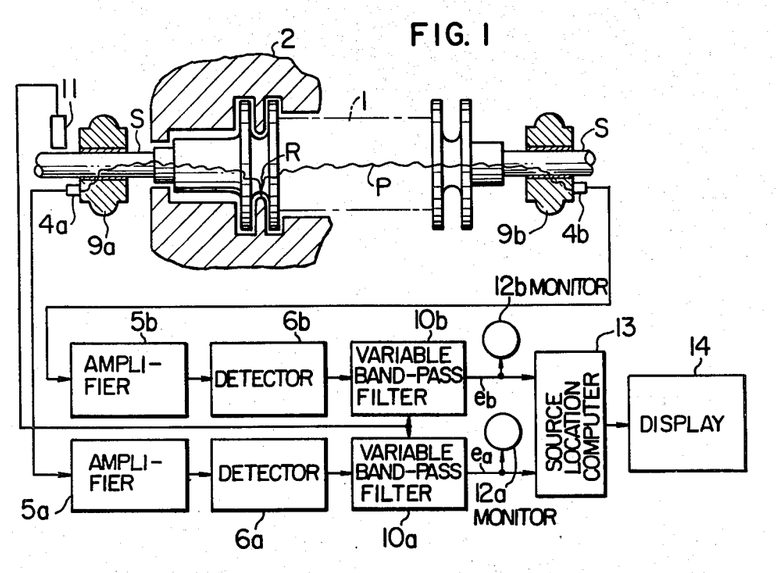
FIG. 1 is a block diagram showing an embodiment of the present invention.

An embodiment of the present invention will now be described with reference to FIG. 1. Referring to FIG. 1, a rotary machine 1, which is herein, for example, a steam turbine, has the rotary shaft S of its rotor journalled in journal bearings 9a and 9b, and two acoustic sensors 4a and 4b are mounted on the journal bearings 9a and 9b, respectively, for detecting an acoustic signal transmitted through the oil film existing between the rotary shaft S and the journal bearings 9a, 9b, FIG. 1 illustrates, for the purpose of explanation, that rubbing is occurring at a point R between the rotor and the stator 2 of the rotary machine 1. The output signals from the acoustic sensors 4a and 4b are detected by detector circuits 6a and 6b after being amplified by amplifiers 5a and 5b and are then applied as input signals to variable band-pass filter circuits 10a and 10b, which per se are well known in the art, respectively. In the meantime, a signal having a frequency proportional to the rotational speed of the rotary machine 1 is optically or magnetically generated by a rotation speed sensor 11 to be applied as a control input signal to the variable band-pass filter circuits 10a and 10b. The output signals from the filter circuits 10a and 10b are applied to monitors 12a and 12b which are, for example, voltmeters, lamps, counters or alarms, and are also applied to a source location computing unit 13. This computing unit 13 computes the location of rubbing on the basis of the input signals and displays the result of computation on a display monitor 14 which is, for example, a cathode-ray tube (CRT) display.

Figure 2:
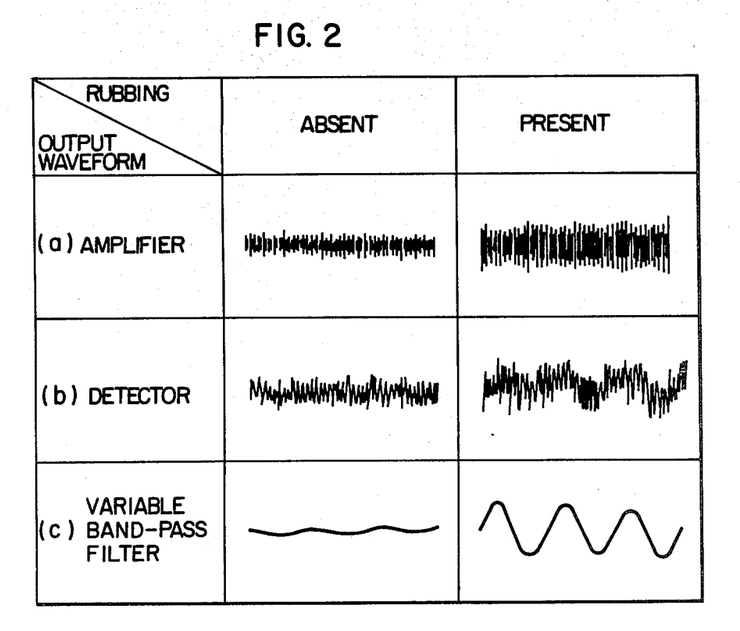
FIG. 2 is a graphic representation of the waveforms of output signals from the individual circuits shown in FIG. 1 to illustrate how the output waveforms vary depending on the absence or presence of rubbing in the rotary machine.
Figure 3:
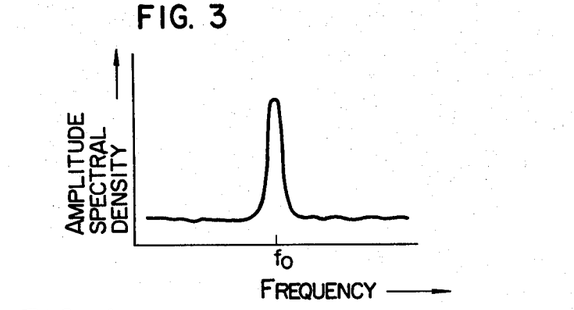
FIG. 3 is a graph showing the result of frequency analysis on the detector output waveform when rubbing is occurring in the rotary machine.

The operation of the embodiment shown in FIG. 1 will now be described. FIG. 2 shows the waveforms of the output signals from the amplifiers 5a, 5b, detector circuits 6a, 6b and variable band-pass filter circuits 10a, 10b when rubbing is present and absent. FIG. 3 shows the frequency characteristic of the output signals from the detector circuits 6a and 6b when occurrence of rubbing is sensed by the acoustic sensors 4a and 4b. It will be seen from FIG. 3 showing the relation between the amplitude spectral density (abbreviated hereinafter as an ASD) and the frequency of the detector output signal that the ASD has its peak at the rotational frequency $f_o$ of the rotary machine, according to the result of frequency analysis. Therefore, band-pass filters, whose passband is made variable depending on the rotational frequency $f_o$ and which per se are well known in the art, are used as the variable band-pass filter circuits 10a and 10b. Thus, the rotational frequency $f_o$ is the center frequency of the passband of these filter circuits 10a and 10b.

Suppose now that the rotational frequency $f_o$ is fixed constant at, for example, 60 Hz. Then, the rotational speed sensor 11 is unnecessary, and it is merely required that a control input signal having such a constant center frequency is continuously applied to the filter circuits 10a and 10b.

In the presence of rubbing, the output signals from the variable band-pass filter circuits 10a and 10b have a waveform as shown in FIG. 2(c). Therefore, the presence or absence of rubbing can be monitored by the monitors 12a and 12b. Although these monitors 12a and 12b may be voltmeters or lamps as described above, they are preferably digital counters so that the number of times of occurrence of the rubbing can be counted.

Figure 4:
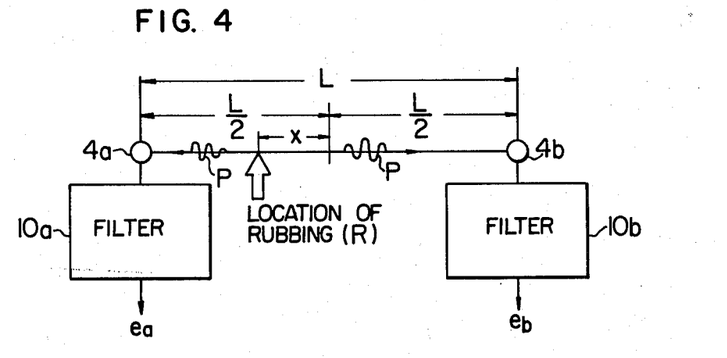
FIG. 4 illustrates how the source of occurred rubbing is located.
Figure 5:
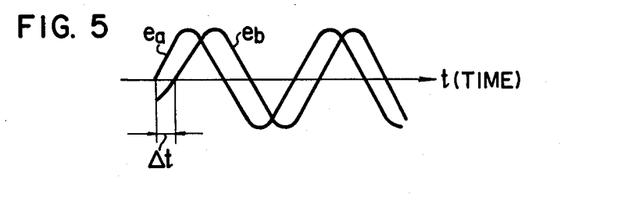
FIG. 5 is a graph showing the waveforms of output signals from the two acoustic sensors shown in FIG. 1.

The function of locating the source of the rubbing will then be described with reference to FIG. 4. Suppose, as shown in FIG. 4, that the acoustic sensors 4a and 4b are spaced apart from each other by a distance L on the rotary shaft S of the rotor of the rotary machine 1, and rubbing is occurring at a point R nearer by a distance x to the acoustic sensor 4a than the acoustic sensor 4b from the center of the distance L. Then, the output waveform $e_b$ of the rotational frequency tuned filter circuit 10b is delayed by a period of time $\Delta t$ relative to that $e_a$ of the filter circuit 10a as shown in FIG. 5. Therefore, by measuring this period of time $\Delta t$, the distance x indicating the point R of rubbing occurrence relative to the center of the distance L can be computed according to the following equation:

$$x = v \cdot \Delta t / 2 \qquad (1)$$

where v is the velocity of sound propagating through the metal.

The rotary machine 1 shown in FIG. 1 is the steam turbine. Suppose that the rubbing signal propagates as a surface acoustic wave along the center hole of the hollow rotary shaft S, the velocity of sound v is $v \approx 3,000$ m/sec, and the distance L between the acoustic sensors 4a and 4b is $L \approx 10$ m, then, the maximum value of $\Delta t$ is about 3.3 msec. Since the rotational frequency $f_o$ is, for example, $f_o = 60$ Hz as described above, the half period is about 8.3 msec. It is therefore possible to measure the time difference $\Delta t$ within this half period.

Figure 6:
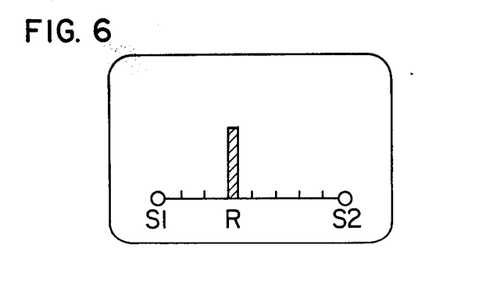
FIG. 6 is a schematic elevation view of a display screen displaying the location of occurred rubbing.

Therefore, when the source location computing unit 13 in FIG. 1 is designed to measure the time different $\Delta t$ and to compute the distance x according to the equation (1), thereby applying the resultant output signal to the display monitor 14 which may be a CRT display, the point R of rubbing occurrence can be monitored on the display monitor 14 as shown in FIG. 6. In FIG. 6, the symbols S1 and S2 indicate the positions of the sensors 4a and 4b respectively, and the symbol R indicates the point of rubbing occurrence corresponding to that shown in FIG. 4.

The variable band-pass filter circuits 10a and 10b may, for example, be voltage-controlled filter circuits. That is, these filter circuits may be such that the filter cutoff frequency is made variable in response to an input voltage which is proportional to the rotational speed of the rotary machine 1.

According to the rubbing detecting apparatus embodying the present invention, the occurrence of rubbing in a rotary machine can be immediately detected, and the point or source of occurrence of rubbing between the rotor and the stator can be reliably located. Therefore, not only is it possible for the occurrence of serious trouble to be prevented before it occurs, thereby greatly contributing to the safety of operation of the rotary machine, but also, serious damage to its component parts can be minimized.

Description will now be directed to the manner of detection of rubbing occurring in a rotary machine, such as a steam turbine, when abnormal metal-to-metal contact occurs simultaneously at one of the bearings of the rotary machine, due to, for example, one of axial alignment between the central axis of the rotary shaft and that of the bearing.

Figure 7A:
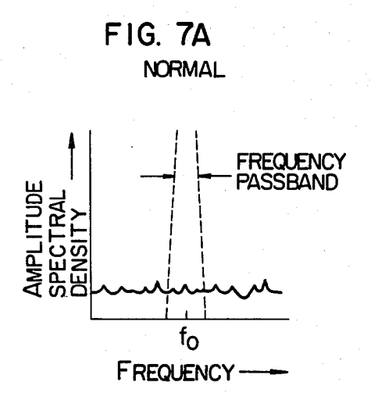
FIGS. 7A to 7D are graphic representation of the results of frequency analysis on the output waveform from a detector circuit detecting a high-frequency abnormal acoustic signal fetched by an acoustic sensor mounted on a bearing of a rotary machine.
Figure 7B:
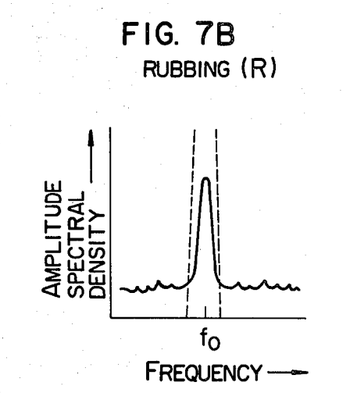
Figure 7C:
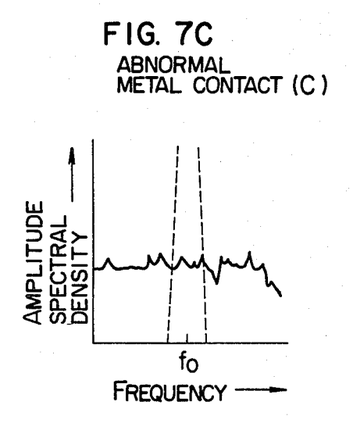
Figure 7D:
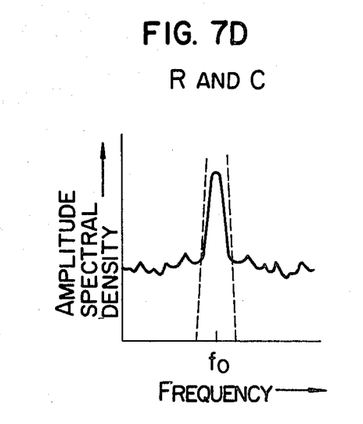

An acoustic sensor was installed on a bearing of a rotary machine, such as a steam turbine, to sense a high-frequency acoustic signal transmitted to the bearing, and the output signal from the acoustic sensor was detected by a detector circuit and was then subjected to frequency analysis. The result of this frequency analysis provided that the amplitude spectral density (ASD) of the detector output signal was low as shown in FIG. 7A when the rotary machine was free from both rubbing and abnormal metal-to-metal contact at the bearing. However, the inventors discovered that, in the event of occurrence of rubbing, this ASD became higher in the rotational frequency passband centered around the rotational frequency $f_o$ of the rotary machine as shown in FIG. 7B, and, in the event of occurrence of abnormal metal-to-metal contact at the bearing, this ASD became generally higher independently of the rotational frequency $f_o$ of the rotary machine as shown in FIG. 7C. The inventors further discovered that, in the event of simultaneous occurrence of rubbing and abnormal metal-to-metal contact at the bearing, the ASD had a waveform representing the combination of the waveforms of FIGS. 7B and 7C, as shown in FIG. 7D.

Another embodiment of the present invention based on the discovery above described is so constructed that the output signal from the acoustic sensor installed on the bearing of the rotary machine is applied to a rubbing detection circuit having the function of extracting only the frequency component representing the rotational frequency $f_o$ of the rotary machine and is applied also to an abnormal metal-to-metal contact detection circuit having the function of extracting the frequency components other than the rotational frequency component, whereby the former and latter circuits detect occurrence of rubbing and occurrence of abnormal metal-to-metal contact at the bearing, respectively.

Figure 8:
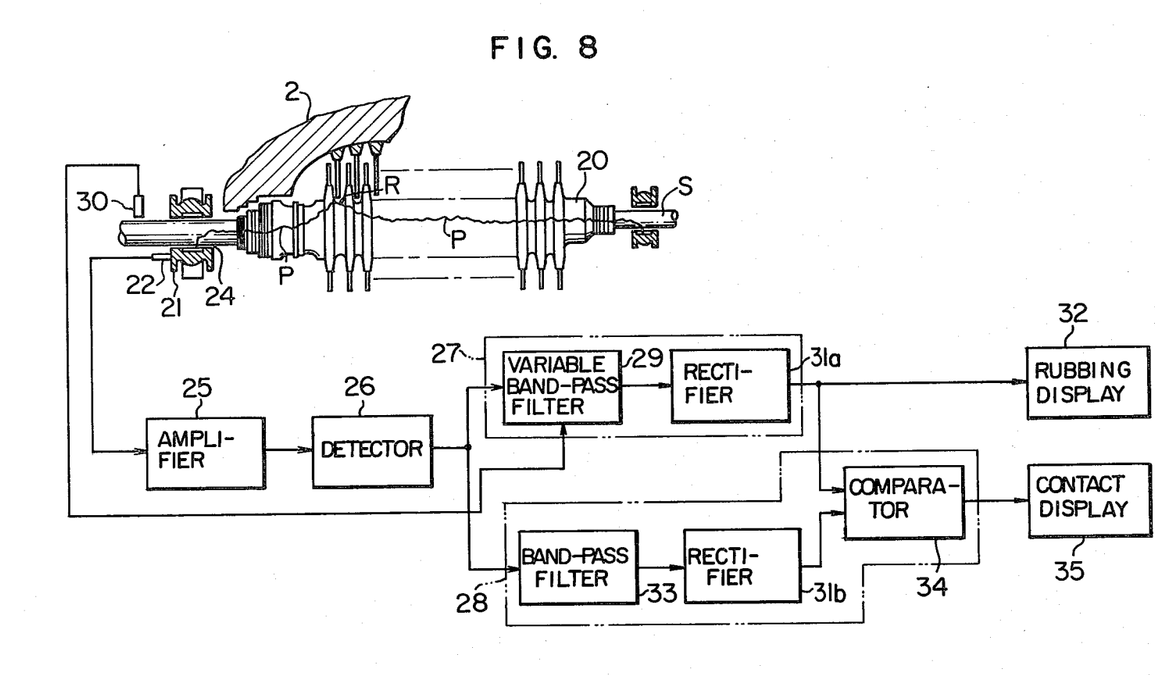
FIG. 8 is a block diagram showing another embodiment of the present invention.

Referring now to FIG. 8 showing the second embodiment of the present invention, a rotary machine 1 such as a steam turbine includes a stator 2 and a rotor 20, and an acoustic sensor 22 is installed on one of bearings 21 supporting the rotary shaft S of the rotor 20. The acoustic sensor 22 is connected at its output terminal to a detector circuit 26 through an amplifier circuit 25. The detector circuit 26 is connected at its output terminal to a rubbing detection circuit 27 which includes a variable band-pass filter circuit 29 and a rectifier circuit 31a, and is connected also to an abnormal metal-to-metal contact detection circuit 28 which includes a low-frequency band-pass filter circuit 33, a rectifier circuit 31b and a comparator circuit 34. A rotational speed sensor 30 provides an output signal synchronous with the rotation of or having a frequency proportional to the rotational speed of the rotor 20 and is connected at its output terminal to the variable band-pass filter circuit 29 in the rubbing detection circuit 27 to apply a control input signal to the filter circuit 29. The rectifier circuit 31a in the rubbing detection circuit 27 is connected at its output terminal to the comparator circuit 34 in the abnormal metal-to-metal contact detection circuit 28 and also to a rubbing monitor 32. The rectifier circuit 31b in the abnormal metal-to-metal contact detection circuit 28 is connected at its output terminal to an abnormal metal-to-metal contact monitor 35 through the comparator circuit 34. The reference numeral 24 designates the oil film in the bearing 21.

Figure 9:
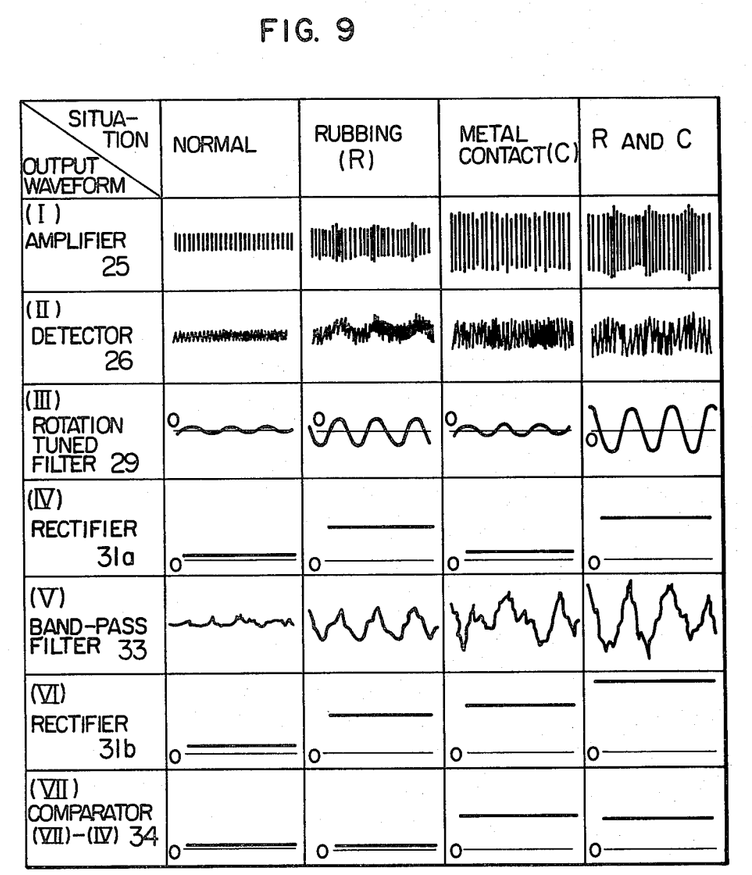
FIG. 9 is a graphic representation of the waveforms of output signals from the individual circuits shown in FIG. 8 to illustrate, for the sake of comparison, how the output waveforms vary depending on the occurrence of rubbing, the occurrence of abnormal metal-to-metal contact at a bearing, or simultaneous occurrence of rubbing and abnormal metal-to-metal contact.

The detecting operation of the second embodiment having the above construction will be described with reference to FIG. 9 showing waveforms of output signals from the circuits 25, 26, 29, 31a, 31b, 33 and 34.

Suppose, for example, that an out of axial alignment condition is present between the central axis of the rotary shaft S of the rotor 20 and that of the bearing 21. Then, an acoustic signal generated due to the out of axial alignment condition between the central axis of the rotary shaft S of the rotor 20 and that of the bearing 21 is transmitted via the bearing material to the acoustic sensor 22. Suppose, on the other hand, that rubbing occurs at a point R between the rotor 20 and the stator 2. Although the rotor 20 and the stator 2 are shown out of contact with each other in FIG. 8 so as to clearly distinguish the rotor 20 from the stator 2, it is assumed that the rotor 20 and the stator 2 are actually in contact with each other at this point R, resulting in occurrence of rubbing at the point R. Then, an acoustic signal generated due to the rubbing contact between the rotor 20 and the stator 2 propagates through the rotor 20 as shown by the line P in FIG. 8 to be transmitted to the acoustic sensor 22 via the oil film 24 in the bearing 21. Consequently, the two acoustic signals, that is, the acoustic signal generated due to the out of axial alignment at the bearing 21 and the acoustic signal generated due to the rubbing contact between the rotor 20 and the stator 2 are simultaneously received by the signal acoustic sensor 22.

The two acoustic signals received by the acoustic sensor 22 are amplified by the amplifier circuit 25 and then detected by the detector circuit 26. FIG. 9(I) shows the waveform of the output signal from the amplifier circuit 25, and FIG. 9(II) shows the waveform of the output signal from the detector circuit 26. The output signal from the detector circuit 26 is applied to the rubbing detection circuit 27 and to the abnormal metal-to-metal contact detection circuit 28.

From the detector output signal applied to the variable band-pass filter circuit 29 in the rubbing detection circuit 27, the rotational frequency component tuned to the rotational frequency of the rotor 20 is only detected under control of the control signal applied to the filter circuit 29 from the rotational speed sensor 30. The output signal from the filter circuit 29 is applied to the rectifier circuit 31a to be converted into an averaged voltage signal which is applied to the rubbing monitor 32.

Thus, the output signal from the variable band-pass filter circuit 29 has a waveform tuned to the rotational frequency of the rotor 20 as shown in FIG. 9(III), and the output voltage from the rectifier circuit 31a rectifying the signal waveform shown in FIG. 9(III) has a level as shown in FIG. 9(IV). In the event of the occurrence of rubbing, the ASD becomes higher in the rotational frequency passband as described already, and the level of the output voltage from the rectifier circuit 31a becomes higher. Therefore, by monitoring the voltage signal applied from the rectifier circuit 31a to the rubbing monitor 32, occurrence of rubbing can be detected as soon as it occurs. Due to the fact that the output signal from the rectifier circuit 31a includes only the signal component tuned to the rotational frequency of the rotor 20, rubbing can be monitored without being affected by the background noise.

On the other hand, in the abnormal metal-to-metal contact detection circuit 28, the detector output signal is applied to the low-frequency band-pass filter circuit 33, and, after converting the output signal from the band-pass filter circuit 33 into an averaged voltage signal in the rectifier circuit 31b, the output signal from the rectifier circuit 31b is applied to the comparator circuit 34. In the comparator circuit 34, the voltage signal applied from the rectifier circuit 31a in the rubbing detection circuit 27 is compared with the voltage signal applied from the rectifier circuit 31b, and the resultant output signal is applied from the comparator circuit 34 to the abnormal metal-to-metal contact monitor 35.

Thus, the output signal from the band-pass filter circuit 33 has a waveform including various low-frequency components as shown in FIG. 9(V), and the output signal from the rectifier circuit 31b rectifying the output signal from the band-pass filter circuit 33 has an averaged voltage level as shown in FIG. 9(VI). The voltage signal from the rectifier circuit 31b includes the rubbing signal component described above. Therefore, this output signal from the rectifier circuit 31b is applied to the comparator circuit 34 to be compared with the output signal from the rectifier circuit 31a, so that the output signal from the comparator circuit 34 provides an averaged voltage level representative of the average of the signal components other than the rotational frequency component, as shown in FIG. 9(VII).

In the event of occurrence of abnormal metal-to-metal contact between the rotary shaft S of the rotor 20 and the bearing 21, the ASD becomes higher throughout the entire frequency range as described already, and the level of the output voltage from the comparator circuit 34 becomes higher as shown in FIG. 9(VII). Therefore, by monitoring the voltage signal applied from the comparator circuit 34 to the abnormal metalto-metal contact monitor 35, the occurrence of abnormal metal-to-metal contact at the bearing 21 can be reliably detected. Because of the fact that the acoustic signal generated due to the abnormal metal-to-metal contact is sensed by the acoustic sensor 22 having high sensitivity, the occurrence of such abnormal metal-to-metal contact at the bearing 21 can be detected as soon as it occurs, in sharp contrast to the prior art manner of detection in which the temperature rise of parts in contact with each other is detected by a thermocouple. According to the present invention, the output signal from the detector circuit 26 is passed through the low-frequency band-pass filter circuit 33 before being applied to the rectifier circuit 31b. Therefore, the signal applied from the comparator circuit 34 to the monitor 35 does not include any high-frequency noise.

The following table represents a classified tabulation of the output signals of the rectifier circuit 31a and comparator circuit 34 applied to the rubbing monitor 32 and abnormal metal-to-metal contact monitor 34, respectively. In the table, the symbols H and L indicate a high output voltage level and a low output voltage level, respectively. It will be seen from the table that the combination of the levels of the voltage signals applied from the circuits 31a and 34 to the respective monitors 32 and 35 is different depending on the trouble-free operation, the occurrence of rubbing, the occurrence of abnormal metal-to-metal contact at the bearing, and simultaneous occurrence of rubbing and abnormal metal-to-metal contact. It is therefore possible to clearly identify the specific situation by comparing the two voltage signals applied by way of the two routes to be displayed on the independent monitors 32 and 35.

TABLE

| Output level | Presence or absense of trouble | | | |
| --- | --- | --- | --- | --- |
| | Trouble-Free | Occurrence of rubbing (R) | Occurrence of metal-to-metal contact (M) | Simultaneous occurrence of R and M |
| Rectifier circuit 31a (FIG. 9(IV)) | L | H | L | H |
| Comparator circuit 34 (FIG. 9(VII)) | L | L | H | H |

In their simplest practical form, the monitors 32 and 35 may be voltmeters or voltage recorders, and their indications may be read to readily identify the specific situation. In another form, the voltage signals applied from the circuits 31a and 34 by way of the two routes may be processed by a logic circuit. In still another form, a microcomputer may be provided to process the output signals from the circuits 31a and 34, and the presence or absence of trouble may be displayed on a display unit.

The embodiment shown in FIG. 8 employs the variable band-pass filter circuit 29 for extracting the rotational frequency component only from the output signal of the detector circuit 26. However, a variable band-pass filter circuit of the so-called reject type designed for detecting only the frequency components other than the rotational frequency component may be employed to exhibit the effect similar to that described with reference to FIG. 8.

The effect may be similar when the acoustic sensor is mounted on, for example, the casing (the pedestal) supporting the bearing.

Figure 10:
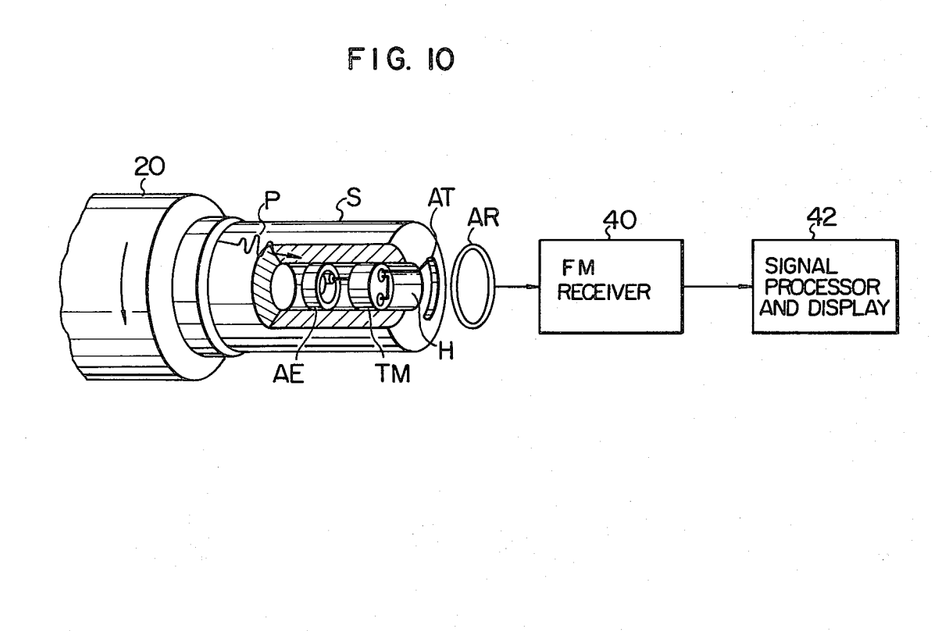
FIG. 10 is a partly cut-away, perspective view showing a modified mounting position of the acoustic sensor in the embodiment shown in FIG. 8.

In the second embodiment, the acoustic sensor 22 sensing the AE signal is installed on the bearing 21. A modification of the second embodiment is shown in FIG. 10. Referring to FIG. 10, an acoustic sensor (an AE sensor) AE is installed in the internal bore H of the rotary shaft S of the rotor 20, and a transmitter unit TM which is an integral assembly of a transmitter module and a power source is disposed together with a transmitting antenna AT in the bore H in the vicinity of the AE sensor AE. In the event of generation of an abnormal acoustic signal P, such an acoustic signal is transmitted in the form of radio wave from the transmitting antenna AT to be received by a receiving antenna AR. An FM receiver 40 is connected to the receiving antenna AR, and a signal processor and display unit 42 is connected to the FM receiver 40 for the purpose of processing and displaying the abnormal acoustic signal P.

The accuracy of trouble detection can be further improved when the acoustic sensor is installed on both the stator 2 and the shaft S of the rotor 20.

It will be understood from the foregoing detailed description of the second embodiment of the present invention that the occurrence of abnormal metal-to-metal contact at a bearing of a rotary machine and the occurrence of rubbing between the stator and the rotor, except the bearings, of the rotary machine can be detected early and simultaneously, so that a danger which may lead to serious damage to or shutdown of the rotary machine can be avoided before it actually occurs. Therefore, not only does the present invention contribute greatly to the safety of operation of the rotary machine, but also it can minimize possible damage to the components of the machine. The present invention is further advantageous in that the capability of detection of the occurrence of abnormal metal-to-metal contact and the occurrence of rubbing by the same apparatus facilitates the maintenance and greatly economizes the costs.

What is claimed is:

1. An apparatus for detecting the occurrence of rubbing in a rotary machine, comprising a rotary machine, at least one acoustic sensor installed on at least one of the rotor part and the stator part of the rotary machine for sensing an acoustic signal generated due to the occurrence of rubbing in the rotary machine, detector means for detecting the output signal from said acoustic sensor, means for fetching a frequency component having a frequency substantially equal to the rotation frequency of the rotary machine from the output signal from said detector means, display means for displaying the output signal from said fetching means, and abnormal metal-to-metal contact detecting means for detecting the occurrence of abnormal metal-to-metal contact at said bearing, said display means including a rubbing display unit displaying the output signal from said rubbing detecting means and an abnormal metal-to-metal contact display unit displaying the output signal from said abnormal metal-to-metal contact detecting means, wherein said rubbing detecting means includes a variable band-pass filter circuit fetching said frequency component from the output signal from said detector means and a first rectifier circuit rectifying the output signal from said variable band-pass filter circuit, and said abnormal metal-to-metal contact detecting means includes a low-frequency band-pass filter circuit receiving the output signal from said detector means, a second rectifier circuit rectifying the output signal from said band-pass filter circuit, and a comparator circuit comparing the output signals from said first and second rectifier circuits.

2. An apparatus according to claim 1, further comprising a rotation speed sensor sensing the rotation speed of the rotary machine, the output signal from said rotation speed sensor being applied to said variable band-pass filter circuit as a control input signal.

3. A method of detecting occurrence of rubbing in a rotary machine, comprising the steps of sensing an acoustic signal generated due to occurrence of rubbing in the rotary machine by at least one acoustic sensor disposed on at least one of the rotor part and the stator part of the rotary machine, detecting the output signal from said acoustic sensor, fetching a frequency component having a frequency substantially equal to the rotation frequency of the rotary machine from said detected signal, and displaying said fetched signal, further comprising the steps of rectifying the signal fetched by said fetching step, displaying said rectified signal on a rubbing display unit as a signal indicative of occurrence of rubbing, processing the signal detected by said detecting step, comparing said processed signal with said rectified signal, and displaying the signal indicative of the result of comparison on an abnormal metal-to-metal contact display unit as a signal indicative of occurrence of abnormal metal-to-metal contact at a bearing.

4. A method according to claim 3, wherein said processing step includes the steps of filtering said detected signal and rectifying said filtered signal.

* * * * *